(12) United States Patent
Tarasev

(10) Patent No.: US 7,790,464 B2
(45) Date of Patent: Sep. 7, 2010

(54) BLOOD HEMOLYSIS ANALYZER

(75) Inventor: Michael Tarasev, Pinckney, MI (US)

(73) Assignee: Blaze Medical Devices, LLC, Ann Arbor, MI (US)

( * ) Notice: Subject to any disclaimer, the term of this patent is extended or adjusted under 35 U.S.C. 154(b) by 795 days.

(21) Appl. No.: 11/744,643

(22) Filed: May 4, 2007

(65) Prior Publication Data

US 2007/0259436 A1 Nov. 8, 2007

Related U.S. Application Data

(60) Provisional application No. 60/746,444, filed on May 4, 2006.

(51) Int. Cl.
G01N 33/72 (2006.01)
(52) U.S. Cl. .................... 436/66; 436/63; 436/164; 435/2; 422/82.05; 422/82.09
(58) Field of Classification Search ............. 436/63, 436/66, 70, 164, 165, 174; 435/2; 422/68.1, 422/82.05, 82.09
See application file for complete search history.

(56) References Cited

U.S. PATENT DOCUMENTS

| | | | |
|---|---|---|---|
| 4,324,556 A * | 4/1982 | Robertson et al. ............. 436/66 |
| 5,330,420 A * | 7/1994 | Lee ............................. 604/6.09 |
| 5,416,026 A * | 5/1995 | Davis ........................... 436/66 |
| 5,685,302 A | 11/1997 | Zikria et al. |
| 5,692,503 A | 12/1997 | Kuenstner |
| 5,720,284 A | 2/1998 | Aoyagi et al. |
| 5,773,301 A | 6/1998 | Ziegler |
| 6,103,197 A | 8/2000 | Werner |
| 6,181,958 B1 | 1/2001 | Steuer et al. |
| 6,284,481 B1 | 9/2001 | Rane et al. |
| 6,294,094 B1 | 9/2001 | Muller et al. |
| 6,304,767 B1 | 10/2001 | Soller et al. |
| 6,623,972 B2 * | 9/2003 | Malin et al. .................... 436/66 |
| 6,989,240 B2 * | 1/2006 | Burns et al. ................ 435/7.25 |
| 2002/0012904 A1 | 1/2002 | Malin et al. |

OTHER PUBLICATIONS

Malinauskas, Richard A. Artificial Organs, vol. 21 (12), 19997, pp. 1255-1267.*

Benesch, R. E., Benesch, R., and Yung, S. (1973), Equations for the Spectrophotometric Analysis of Hemoglobin Mixtures, Anal Biochem 55, 245-8.

Van Assendelft, O. W., and Zijlstra, W. G. (1975), Extinction Coefficients for Use in Equations for the Spectrophotometric Analysis of Haemoglobin Mixtures, Anal Biochem 69, 43-8.

Latimer, P., Moore, D., Bryant F. (1968), Changes in Total Light Scattering and Absorption Caused by Changes in Particle Conformation, J. Theor. Biol, 23:348-67.

(Continued)

*Primary Examiner*—Maureen M Wallenhorst
(74) *Attorney, Agent, or Firm*—Jelic Patent Services, LLC; Stanley E. Jelic

(57) ABSTRACT

Systems and methods for determining the concentration of hemoglobin derivatives in bodily fluids include devices for measuring and comparing the absorption of electromagnetic radiation by cellular and cell-free hemoglobin at two or more wavelengths in the Soret region. Systems and methods for determining erythrocyte membrane fragility include devices for measuring the concentration of at least one cell-free hemoglobin derivative, and using the absorption properties of cellular and cell-free hemoglobin derivatives in the Soret region.

22 Claims, 4 Drawing Sheets

OTHER PUBLICATIONS

Schneider, A. S., Harmatz, D. (1976), An Experimental Method for Absorption Flattening and Scattering in Suspensions of Absorbing Particles: Circular Dicroism and Absorption Spectra of Hemoglobin In Situ in Red Blood Cells, Biochem. 15:4158-62.

* cited by examiner

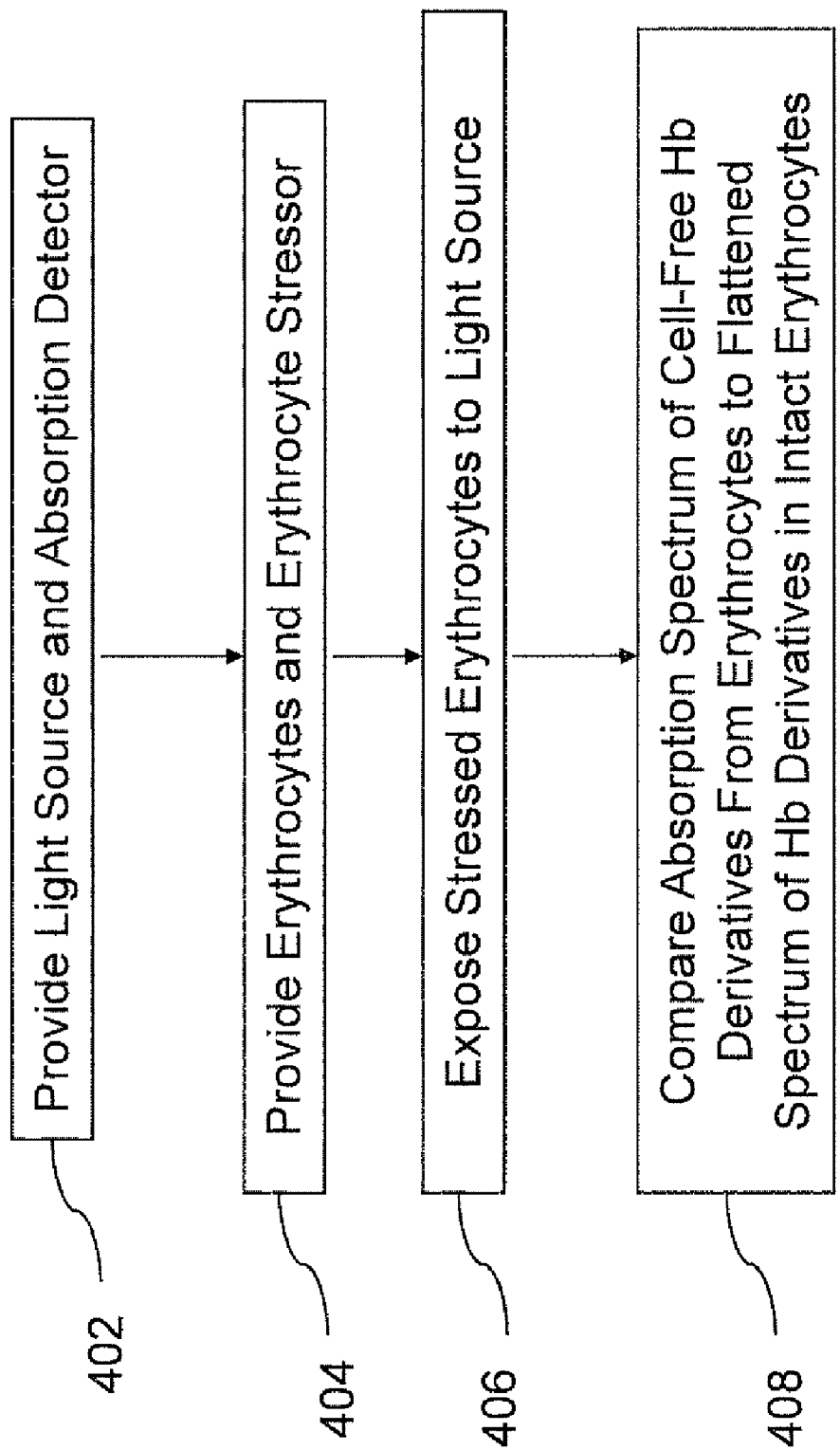

ial Application No. 60/746,444 filed on May 4, 2006, the entirety of which is incorporated herein by reference.

BLOOD HEMOLYSIS ANALYZER

RELATED APPLICATIONS

This invention claims priority to and the benefit of U.S. Provisional Application No. 60/746,444 filed on May 4, 2006, the entirety of which is incorporated herein by reference.

TECHNICAL FIELD

This invention relates generally to devices and methods that are used for measuring the concentration of hemoglobin in bodily fluids such as blood, plasma, serum and urine. In addition, the invention provides methods and devices for evaluating erythrocyte membrane deformation or fragility, erythrocyte hemolysis and hemocrit levels in a fluid sample.

BACKGROUND OF THE INVENTION

Erythrocytes (red blood cells or RBCs), leukocytes (white blood cells), and platelets comprise the cellular constituents of mammalian blood. Healthy nonpathological erythrocytes are flexible, biconcave disks that lack both nuclei and mitochondria. Erythrocytes contain an allosteric, iron-containing metalloprotein called hemoglobin (Hb), that binds oxygen and carbon dioxide and enables erythrocytes to transport these gases in the blood. Hemoglobin consists of four subunits, each containing a nonprotein heme group surrounded by the globin protein portions of the molecule. Each heme group contains an iron (Fe) atom held in the center of a heterocyclic porphyrin ring. Like all heme-containing proteins, Hb absorbs electromagnetic radiation in the visible and near ultraviolet (UV) portions of the spectrum. This characteristic allows Hb to be detected and quantified using spectrophotometric methods.

The iron atom of the Hb contained within erythrocytes exists in either oxidation state $Fe^{2+}$ or $Fe^{3+}$. Iron in the $Fe^{2+}$ state binds oxygen and forms oxyhemoglobin (Oxy-Hb) in the pulmonary capillaries of the lungs. Other gas molecules compete with oxygen for the heme binding site and form heme derivatives. Notably, carbon monoxide binds the heme iron in the $Fe^{2+}$ state and forms carboxyhemoglobin (CO-Hb), reducing the Hb available for oxygen transport. Deoxyhemoglobin (Doxy-Hb), the reduced ($Fe^{2+}$) state of Hb with no bound oxygen, is formed after the oxygen is released to the tissues. Oxidation to the $Fe^{3+}$ state converts hemoglobin to methemoglobin (Met-Hb), which cannot bind oxygen. Oxy-Hb and Doxy-Hb comprise about 90% of the total Hb in blood.

Although hemoglobin exists largely within the erythrocytes, healthy blood plasma contains a small amount of cell-free Hb, usually less than 0.05% of total hemoglobin. However, the cell-free Hb levels sometimes increase significantly in response to pathological hemolytic conditions such as sickle cell anemia, paroxymal hemoglobinuria, acute autoimmune hemolytic anemia, transfusion reactions due to blood group incompatibilities and faulty intracardiac valvular prostheses. Medical procedures requiring manipulation of the blood such as dialysis, or cardiac bypass procedure can also cause hemolysis. It is therefore sometimes medically important to have a rapid and inexpensive method to measure plasma hemoglobin.

Healthy erythrocytes are biconcave cells that have sufficiently elastic membranes to allow the erythrocyte to elongate and pass through the capillaries within the circulatory system. Blood for transfusion is commonly stored for several weeks under refrigeration with an anticoagulant such as heparin, citrate or an anticoagulant and preservative such as CPDA-1. During storage, erythrocyte membranes lose their elasticity and become fragile and prone to rupture during handling or after it the blood given to a patient. It is therefore sometimes desirable to determine erythrocyte membrane elasticity before using the stored blood to transfuse a patient.

In medical practice, the plasma cell-free Hb level is determined by obtaining a sample of blood and adding an anticoagulant, usually heparin. The cellular fraction is precipitated by centrifugation and the plasma is removed. An estimate of cellular erythrocyte hemoglobin can be obtained by determining the hematocrit, the packed red cell volume. The plasma is analyzed for cell-free hemoglobin content either by enzymatic or spectrophotometric methods. The enzymatic methods rely on using the pseudo-peroxidase activity of Hb to act upon a substrate such as benzedine, parpminobenzoic acid or tetramethylbenzidine to produce readily quantifiable reaction products.

Several spectrophotometric methods to determine plasma concentrations of cell-free Hb have been described. One such method requires derivatizing most forms of hemoglobin with Drabkin's reagent and forming cyanomethemoglobin, which has an absorbance peak at 540 nm wavelength. Other methods allow direct measurement of plasma hemoglobin concentration by scanning spectroscopic methods using visible and near infrared portions of the electromagnetic spectrum. Any of these methods can also be used to evaluate the relative amount of ruptured erythrocytes thus providing an indirect measure of erythrocyte membrane fragility, based on cell-free Hb concentration in plasma. However not all changes in membrane fragility result in erythrocyte rupture and increased cell-free Hb. In addition, all of these methods share the limitation that centrifugation to remove the erythrocytes is required before analysis can take place, and thus, require access to laboratory equipment and do not provide the speed necessary for rapid analysis.

It would be desirable, to provide a system and method for measuring the concentration of Hb in bodily fluids such as blood, plasma, serum, and urine without having to remove erythrocytes and other cellular components, and without requiring that chemical or enzymatic reactions be conducted. Such a system and method would overcome many of the limitations and disadvantages inherent in those described above.

SUMMARY OF THE INVENTION

One aspect of the present invention provides a system for measuring the concentration of cell-free Hb derivatives in a biological sample that contains erythrocytes. The system includes a light source configured to emit light, and a sample block configured to allow light having a wavelength of about 390-460 nm to pass through the sample. A first portion of the light is absorbed by the cell-free Hb derivatives and a second portion is absorbed by the Hb derivatives contained within the erythrocytes. The system further includes one or more absorption detectors configured to detect light absorption by the sample and a processor configured to compare the change in light absorption at two or more wavelengths and thereby determine the concentration of the cell-free Hb derivatives.

Another aspect of the invention provides a method for measuring the concentration of cell-free hemoglobin species in a biological sample including erythrocytes. The method includes providing a sample, a light source, and an absorption detector capable of detecting light having a wavelength of about 390-460 nm. The method further includes passing the light through the sample and detecting absorption of the light by the sample, and comparing the absorption spectrum of the sample at two or more wavelengths in order to determine the concentration of one or more cell-free Hb derivatives in the sample.

Another aspect of the invention provides a system for measuring the fragility of erythrocyte membranes in a biological sample. The system includes a light source, and a device configured to apply a defined stress to the membranes of the erythrocytes in the sample as the sample is passed through the device. The system further includes a sample block configured to allow light having a wavelength of about 390-460 nm to pass through the sample. A first portion of the light is absorbed by the cell-free Hb derivatives and a second portion is absorbed by the Hb derivatives contained within the erythrocytes. The system further includes one or more absorption detectors configured to detect light absorption by the sample, and a processor configured to compare the change in light absorption at two or more wavelengths, and thereby determine the concentration of the cell-free Hb derivatives, and fragility of erythrocyte membrane.

Yet another aspect of the invention provides a method for measuring erythrocyte membrane fragility in a biological sample. The method includes providing a light source, a sample including erythrocytes, an erythrocyte stressor configured to apply a controlled amount of stress to the cellular membranes of the erythrocytes, and a detector configured to detect light absorption within the wavelength range of about 390-460 nm. The method further includes subjecting the erythrocytes in the sample to a defined stress, passing light through the sample, and comparing the absorption spectrum of cell-free Hb derivatives in the sample to a flattened absorption spectrum of the Hb derivatives contained within the erythrocyte, and thereby determining the fragility of the erythrocyte membranes.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

BRIEF DESCRIPTION OF THE DRAWINGS

FIG. 4 is a flow diagram of a method for determining erythrocyte membrane fragility, in accordance with the present invention.

DETAILED DESCRIPTION

Throughout this specification, like numbers refer to like structures.

The iron porphyrin ring structure of Hb absorbs electromagnetic radiation in the Soret (350-450 nm), visible (500-600 nm), and near-IR (600-750 nm) portions of the spectrum. Within each of these portions of the spectrum, each Hb derivative has an absorption maximum that is characteristic of that compound, although the molar extinction coefficients for the Hb derivatives within each wavelength range differ. Although the molar extinction coefficients within the visible region are fairly low, there is generally little interference from other non-heme compounds in biological samples, making the visible range a preferred choice for analytical methods in the prior art.

In the Soret region (305-450 nm), the molar extinction coefficients of most heme-containing compounds are higher than in the visible or near infrared regions. However, in blood, most Hb derivatives are contained within the erythrocytes, resulting in an uneven distribution of Hb derivatives between the erythrocytes, having a high concentration of Hb, and the plasma, having a very low concentration. The uneven distribution causes an apparent decrease in absorbance by the erythrocyte Hb, compared to the absorbance due to cell-free Hb. The apparent decrease in absorbance is reflected in a flattened absorbance spectrum for erythrocyte Hb, in which the absorbance at each wavelength is lower than the absorbance for an equal concentration of Hb were it distributed homogenously throughout the solution. Because of lower extinction coefficients for Hb derivatives in the visible range above 500 nm, absorption spectra of cellular Hb are not significantly flattened in the visible range. One embodiment of the present invention utilizes the differences in magnitude of the absorption spectra of cellular Hb derivatives and cell-free Hb derivatives to quantify low concentrations of cell-free Hb derivatives in the presence of much larger amounts of cellular Hb.

The medically significant Hb derivatives are Oxy-Hb, which is formed in the lungs when oxygen is bound to the heme groups, Deoxy-Hb, the reduced form of Hb that arises after oxygen is released to the cells, CO-Hb, which has a carbon monoxide molecule bound to the heme group, and Met-Hb, the oxidized form of Hb. Each of these Hb derivatives has a characteristic absorption maximum within the Soret region, as indicated in the following table:

| Hemoglobin Derivative | Maximum Absorbance (nm) |
| --- | --- |
| Met-Hb | 405 |
| Oxy-Hb | 415 |
| CO-Hb | 419 |
| Deoxy-Hb | 430 |

Absorbance at these peak wavelengths can be used to identify the hemoglobin derivatives in a sample.

Figure 1:
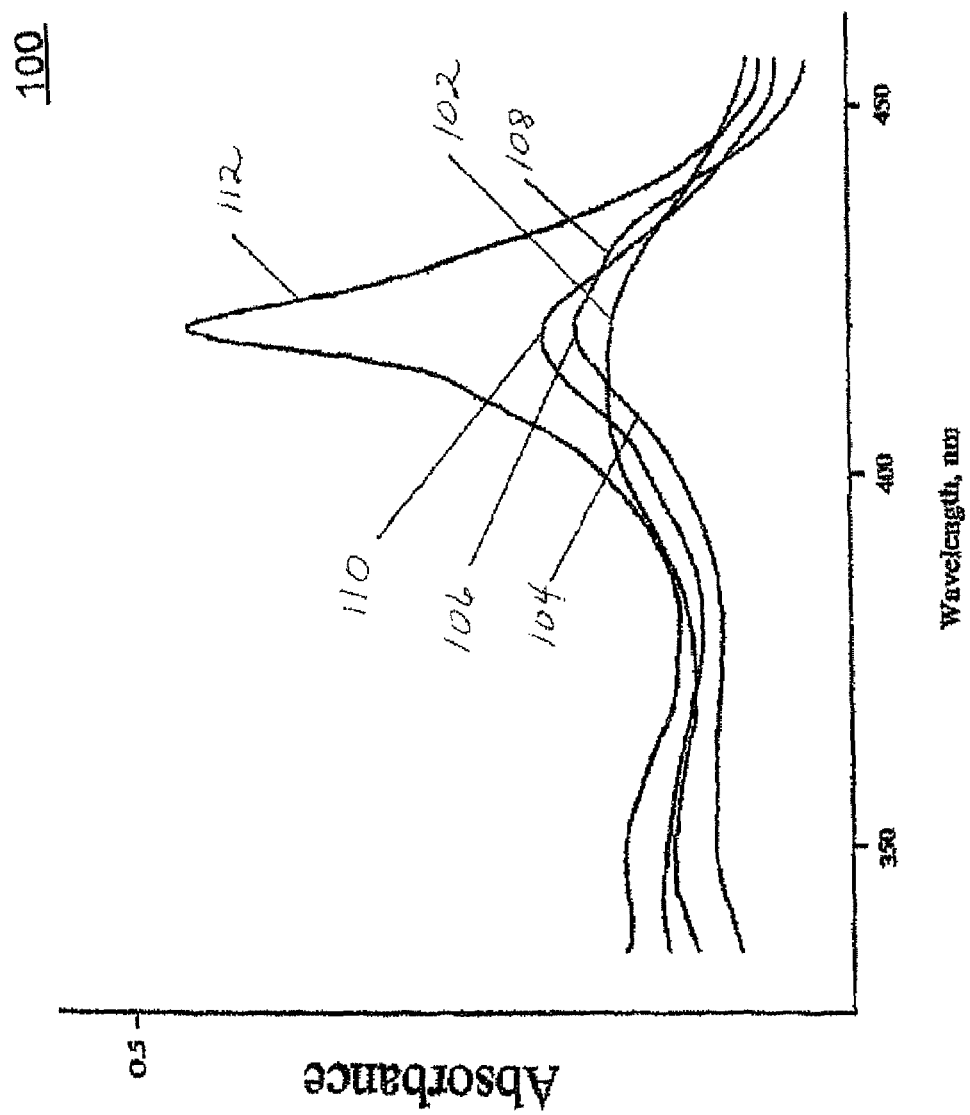
FIG. 1 is a graphical representation of the absorption spectra of Hb derivatives in blood and cell-free Hb derivatives at wavelengths of 350-460 nm.

FIG. 1 is a graphical representation 100 of the absorption spectra of blood samples comprising erythrocyte Hb derivatives, and cell-free Hb derivatives at wavelengths of 350-460 nm. In this graph, light absorbance (y axis) is plotted versus wavelength (x axis). Absorption spectrum 102 is the broad, flattened spectrum of blood in which the Hb derivatives are predominantly within the erythrocytes. Absorption spectrum 104 is the spectrum of partially hemolyzed blood, and comprises the composite absorption due to both erythrocyte Hb and cell-free Hb. The maximal absorption 106 occurs at wavelength 419 nm, indicating the presence of CO-Hb. In addition, a small secondary absorption peak 108 occurs at approximately wavelength 430 nm, and indicates the presence of Deoxy-Hb in the sample. Absorption spectrum 110 is the spectrum of partially hemolyzed blood, and has a maximal absorbance at wavelength 419 nm due to the presence of erythrocyte CO-Hb and cell-free CO-Hb in the sample. Absorption spectrum 112 is the spectrum of blood that has been fully hemolyzed, and only cell-free Hb derivatives are present. Spectrum 112 has an absorption maximum at approximately 419 nm, indicating that a substantial amount of CO-Hb is present in the sample. In addition, small secondary peaks are present at 405 nm and 430 nm, indicating, respectively, that met-Hb and deoxy-Hb are also present in the sample.

Figure 2:
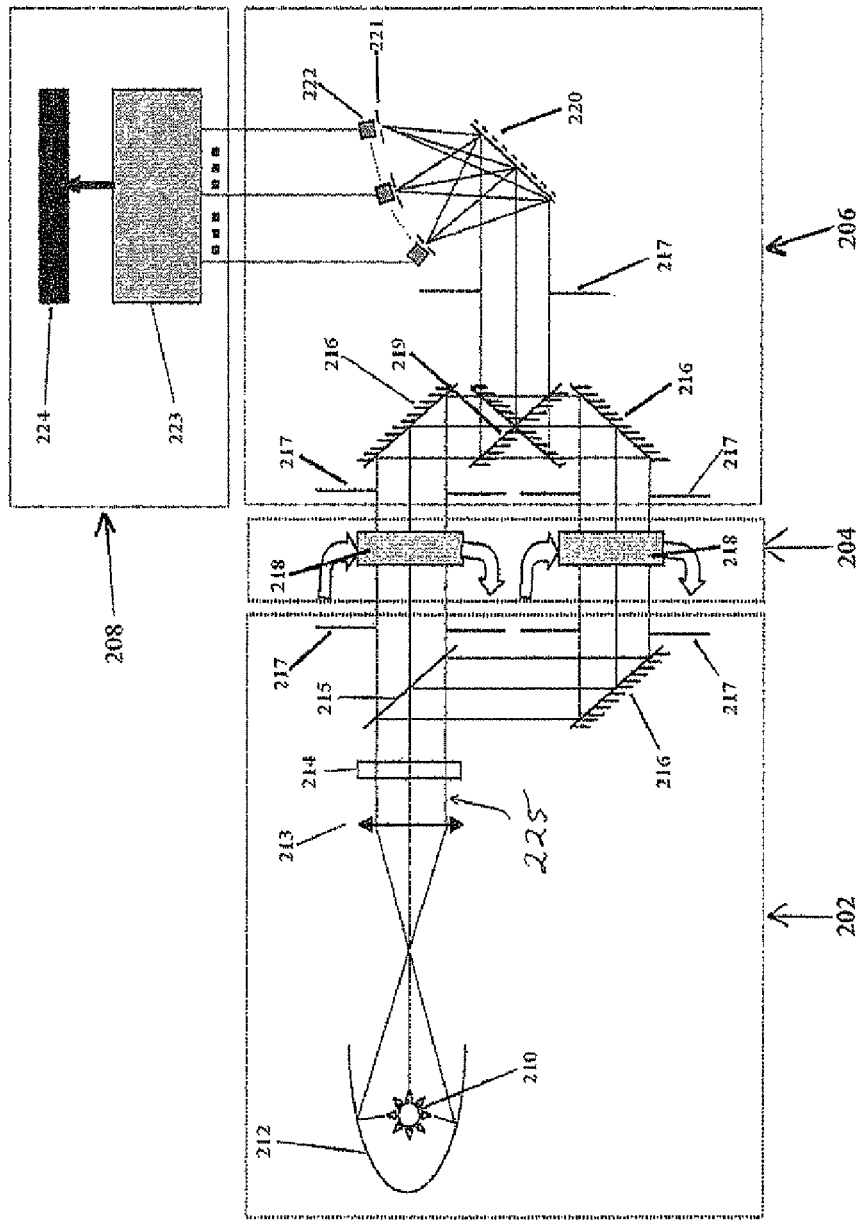
FIG. 2 is a schematic illustration of a device for measuring absorption of electromagnetic radiation by Hb containing biological samples, in accordance with the present invention.

FIG. 2 is a schematic illustration of an exemplary embodiment of a system 200 for measuring the absorption of electromagnetic radiation by Hb derivatives in biological samples, in accordance with the present invention. The system includes light block 202, sample block 204, detection block 206, and signal processing block 208.

Light block 202 further includes a power supply (not shown) connected to light source 210. Light source 210 emits light in the ultraviolet and visible ranges of the electromagnetic spectrum. Focusing mirror 212 partially surrounds light source 210 and focuses the light so that an incident beam 225 of light is directed to collimating optics system 213. Optics system 213 directs the rays of light so that the rays are parallel to each other, and are directed toward filters 214. Filters 214 block light in spectral regions such as short to medium range ultraviolet and infrared that are not used in the analysis. In one embodiment, light block 202 includes beam splitter 215, mirrors 216, and one or more exit and entry slits 217. These devices direct the light beam into two separate, parallel paths as it passes into sample block 204.

Sample block 204 provides a device to introduce the sample to be analyzed into the path of incident light beam 225. In one embodiment of the invention, sample block 204 includes one or more quartz cuvettes or blood transfusion tubes, and a bracket that holds the cuvettes or transfusion tubes securely in the path of light beam 225. In one embodiment of the invention, the cuvettes or transfusion tubes provide a sample thickness of 0.05-0.5 mm. The required sample thickness is determined by the hematocrit. In another embodiment, two fiber optic guides are placed in optical contact, and a small amount of sample is placed between the guides. This arrangement allows the sample thickness to be optimized by the position of the fiber optic guides relative to each other during the analysis. In another embodiment, sample block 204 includes one or more flow through cuvettes 218. In another embodiment, the portion of flow through cuvette 218 that is situated in light beam 225 is surrounded by and integration sphere. As shown in FIG. 2, incident light beam 225 is split by beam splitter 215, and is directed so that one portion of incident light beam 225 passes through each of two flow through cuvettes 218 and into detection block 206. In one embodiment, detection block 206 analyzes each beam alternately, allowing for rapid analysis and comparison of the two beams.

Detection block 206 includes entry and exit slits 217 coupled with mirrors 216, that together focus the light beam on turning mirror 219, which in turn, directs the light beam to a dispersion element that disperses light of different wavelengths over a defined area. In one embodiment, the dispersion element is defraction grating 220. In another embodiment, the light is focused by either the defraction grating 220 or another focusing element and the detector 222 is positioned at the focal point of light at each wavelength of interest. In one embodiment, the defracted light falls on a series of slits 221 that are arranged so that light having the wavelength of interest passes through slits 221 and impinges on detectors 222. Detectors 222 generate a signal in response to the received light and send the signal to signal processing block 208.

Signal processing block 208 includes signal amplifiers, and appropriate logic circuits for signal correction 223, to produce and record signal 224. In one embodiment of the invention, signal amplitudes are processed using multi-wavelength analysis algorithms. In another embodiment, a dedicated, programmed, processor is employed. In yet another embodiment the signals are analyzed externally in a computer using appropriate software programs.

Figure 3:
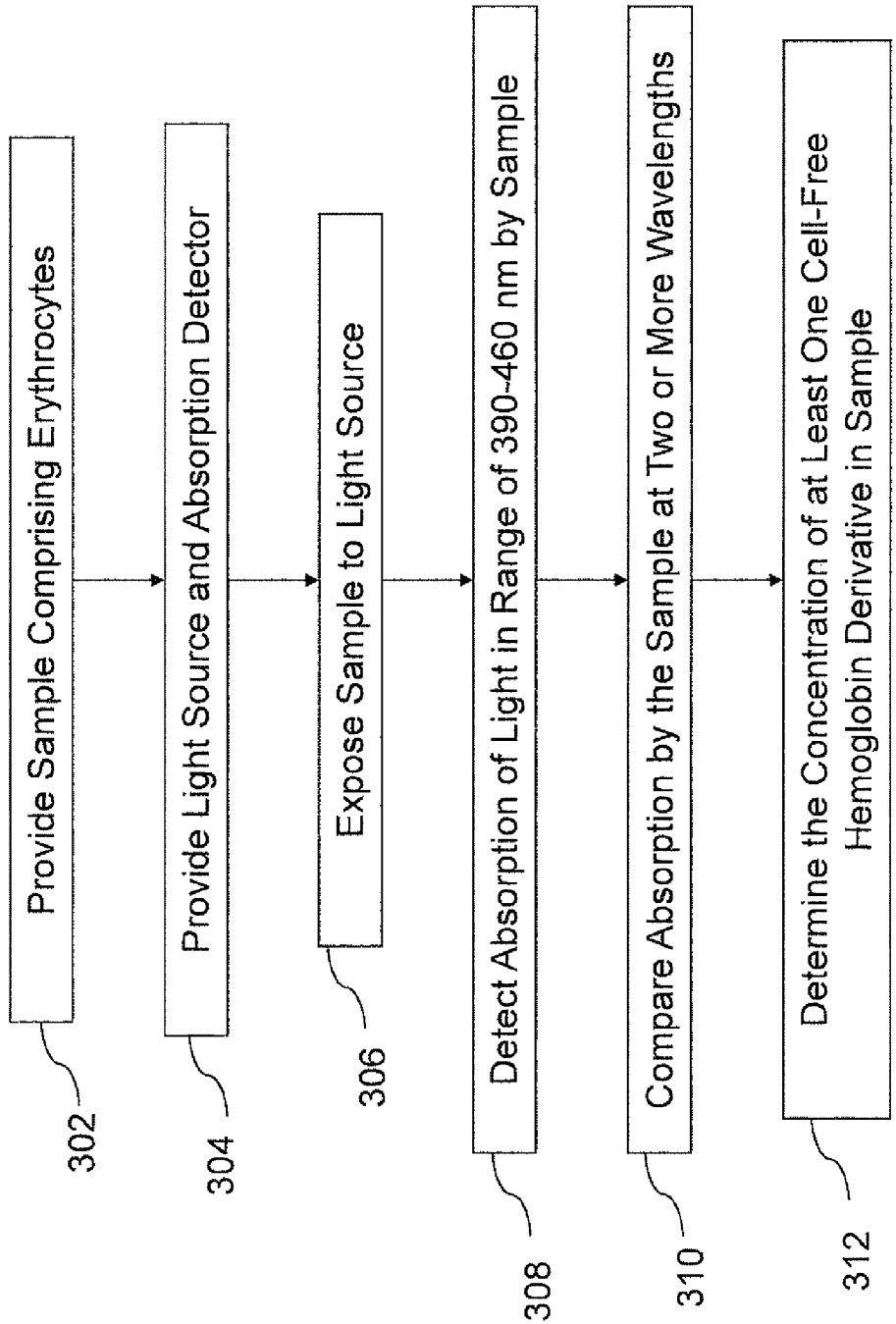
FIG. 3 is a flow diagram of a method for measuring the concentration of one or more cell-free Hb derivatives in a biological sample containing erythrocytes, in accordance with the present invention.

FIG. 3 is a flowchart of method 300 method for measuring the concentration of one or more cell-free Hb derivatives in a biological sample containing erythrocytes, in accordance with the present invention. As indicated in Block 302, any sample of biological fluid, such as whole blood, anticoagulated blood, preserved blood, blood products, plasma, serum, and urine may be analyzed. In medical practice, it is sometimes desirable to analyze blood that has been stored for a period of time before using it to transfuse a patient. Blood products are treated with anticoagulants and preservatives such as citrate phosphate dextrose (CPD), citrate phosphate dextrose adenine (CPDA-1), and solutions known in the art as AS-1, AS-3 and AS-5. Despite the precautions taken, cell-free Hb levels increase with time during storage, and erythrocyte membranes become more fragile and prone to rupture. Renal dialysis, cardiac bypass procedure, blood photodynamic therapy, or other medical procedures requiring external manipulation of the patient's blood are known to increase erythrocyte rupture and consequently cell-free Hb. As a result, a real time evaluation of the patient's blood is needed. In one embodiment of the invention a portion of the patient's blood is diverted to a flow cell of the system shown in FIG. 2 for analysis, while the patient is undergoing a procedure requiring external manipulation of the blood.

To analyze a blood sample, a light source and one or more absorption detectors are needed, as indicated in Block 304. In one embodiment of the invention, a system such as shown in FIG. 2 is used. In one embodiment, a suitable light source is a deuterium arc lamp. The sample is placed in a quartz cuvette or a flow through sample cell and positioned in the light beam, as indicated in Block 306.

As the light beam passes through the sample, a portion of the electromagnetic energy of the light beam is absorbed by the Hb derivatives in the sample. The light beam is then directed to an array of detectors that detect electromagnetic energy in the wavelength range of 390-460 nm. In one embodiment of the invention, the light beam is split by a beam splitter, and the light beam is passed through two cells, one of which (sample cell), contains the sample to be analyzed, and the other (reference cell) contains water, or any other appropriate substance that does not absorb in the 390-460 nm wavelength range. In another embodiment, the reference cell is used to correct for light scattering and/or the flattened absorbance due to Hb derivatives contained in erythrocytes. In this case, the reference cell would contain unstressed erythrocytes and the sample cell would contain stressed erythrocytes. In another embodiment, the reference cell would contain a plasma free sample, in which the volume of plasma has been replaced by an optically clear solution that preserves the erythrocytes intact. The detector or detectors compare the portion of the light beam that passed through the sample with the portion that passed through the reference material, and detects the reduced electromagnetic energy in the 390-460 nm range that was absorbed by the sample, as indicated in Block 308.

The above comparison is made by the detector(s) at two or more wavelengths in the 390-460 portion of the spectrum, as indicated in Block 310. In one embodiment of the invention, the difference in absorption is determined at the wavelength at which the peak absorbance occurs, at one wavelength that is longer than the wavelength of peak absorption, and at one wavelength that is shorter than the wavelength of peak absorption. By comparing the change in absorption at these three points, the steepness of the absorption curve can be assessed. A steep absorption curve is characteristic of cell-free Hb derivatives, while a broad, flattened curve with no single absorbance maximum is characteristic of Hb contained within erythrocytes. The concentration of the cell-free Hb derivatives can be determined, as indicated by Block 312.

In one embodiment of the invention, the concentrations of the Hb derivatives are calculated using multiwavelength analysis and the formula:

$$Absorbance^k = \sum_n \varepsilon_n^k c_n l$$

where $\varepsilon_n^k$ is the extinction coefficient of the hemoglobin form n at wavelength k, $c_n$ is the molar concentration of the form n, and l is the light path length through the sample. The values of the molar extinction coefficients of each of the Hb derivatives are known in the art. In one embodiment, the wavelengths corresponding to the absorbance maxima of each of the Hb derivatives are selected for analysis. The solution is obtained using the Gaussian elimination method or other appropriate methods. In one embodiment, absorption at additional wavelengths is analyzed in order to increase the accuracy of the method. Additional wavelengths to be used are selected to obtain maximum sensitivity of the analysis and maximize the ability to distinguish among the Hb derivatives. Using these methods, the absorbance of a sample containing both cell-free Hb derivatives and Hb derivatives contained within erythrocyates can be analyzed. The flattened absorbance spectrum of the cellular Hb derivatives is subtracted from the total absorbance, and the concentration of cell-free Hb derivatives can be determined from the difference. By selecting the Soret region of the electromagnetic spectrum, where the difference between the absorbance of cellular Hb (flattened spectrum) and the absorbance of cell-free Hb (high extinction coefficient) is maximal, this method allows quantification of a very small amount of cell-free Hb in the presence of a much larger amount of Hb derivatives in erythrocytes. In contrast, in the visible range of the electromagnetic spectrum, cell-free and cellular Hb could not be differentiated because both have identical observed spectra.

FIG. 4 is a flowchart of method 400 for determining erythrocyte membrane fragility, in accordance with the present invention. As indicated in Block 402, a light source and absorption detector are needed. In one embodiment of the invention, a system such as that shown in FIG. 2 is used for analysis, and supplies each of these elements. In addition a device for applying a defined stress to the erythrocyte membranes is used, as indicated in Block 404. The stressor may be osmotic or mechanical, usually shear force, and when applied to the erythrocyte, causes the cellular membrane to lyse, and the cellular contents, including Hb derivatives to be released, increasing the amount of cell-free Hb derivatives. In one embodiment, the stressor is mechanical, so that the concentration of each of the Hb derivatives is unchanged by the analytic procedure. In another embodiment, an osmotic stressor is used which causes changes in hematocrit requiring appropriate correction. By progressively increasing the amount of either osmotic or shear stress applied to the sample an erythrocyte membrane fragility index, defined as the amount of force (osmotic or shear) required to lyse 50% of the erythrocytes can be calculated. In addition a sample fragility profile defined as the dependence of the fraction of erythrocytes lysed on the amount of force (osmotic or shear) applied to the sample.

Next, the stressed erythrocytes are placed in the path of the light beam (Block 406), and the amount of absorption in the 390-460 nm region of the electromagnetic spectrum is determined. Finally, the absorption spectrum of the cell-free Hb derivatives released from the erythrocytes is compared to the flattened spectrum of the Hb derivatives in intact erythrocytes. In one embodiment of the invention, the comparison is made using multi-wavelength analysis. In another embodiment of the invention, the spectrum obtained from the sample before the stressor is applied is compared to the spectrum of the stressed sample, and the increase in the amount of cell-free Hb derivatives is determined.

While the invention has been described with reference to particular embodiments, it will be understood by one skilled in the art that variations and modifications may be made in form and detail without departing from the spirit and scope of the invention.

The invention claimed is:

1. A system for determining cell-free hemoglobin concentration within a sample containing at least one cell-free hemoglobin derivative and at least one cellular hemoglobin derivatives contained within erythrocytes, the system comprising:
   a light source configured to emit light;
   a sample block containing the sample and configured to allow the light to pass through the sample wherein, a first portion of the light, having a wavelength of about 390-460 nm, is absorbed by the cell-free hemoglobin derivatives, and a second portion of the light, having a wavelength of about 390-460 nm, is absorbed by the cellular hemoglobin derivatives contained within erythrocytes;
   at least one absorption detector configured to determine the light absorption of the sample block containing the sample, within a wavelength range of about 390-460 nm, and to generate a flattened spectra of cellular hemoglobin derivatives contained within erythrocytes and a non-flattened spectra of cell-free hemoglobin derivatives; and
   a processor configured to use data from the absorption detector to compare the flattened spectra of cellular hemoglobin derivatives contained within erythrocytes to the non-flattened spectra of cell free hemoglobin derivatives determined from the change in the light absorption of the sample within a wavelength range of 390-460 nm, and thereby determine the cell free hemoglobin concentration within the sample.

2. The system of claim 1 wherein the hemoglobin derivatives are selected from the group consisting of oxyhemoglobin, deoxyhemoglobin, carboxyhemoglobin, and methemoglobin.

3. The system of claim 1 wherein the sample is a biological fluid selected from the group consisting of whole blood, anticoagulated blood, preserved blood, blood products, plasma, serum, and urine.

4. The system of claim 1 wherein the first portion of light is absorbed by the cell-free hemoglobin derivatives providing an absorbance spectrum characteristic of hemoglobin in solution, and the second portion of light is absorbed by cellular hemoglobin derivatives contained within erythrocytes providing a flattened absorption spectrum characteristic of cellular hemoglobin derivatives.

5. A method for determining cell-free hemoglobin concentration within a sample containing at least one cell-free hemoglobin derivative and at least one cellular hemoglobin derivative contained within erythrocytes, the method comprising:
projecting light with a light source configured to emit light into a sample block containing the sample and configured to allow the light to pass through the sample wherein, a first portion of the light, having a wavelength of about 390-460 nm, is absorbed by the cell-free hemoglobin derivative, and a second portion of the light, having a wavelength of about 390-460 nm, is absorbed by the cellular hemoglobin derivative contained within erythrocytes;
measuring the light absorption with at least one absorption detector configured to determine the light absorption of the sample block containing the sample, within a wavelength range of about 390-460 nm, and to generate a flattened spectra of cellular hemoglobin derivatives contained within erythrocytes and a non-flattened spectra of cell-free hemoglobin derivatives; and
utilizing a processor to compare the flattened spectra of cellular hemoglobin derivatives contained within erythrocytes to the non-flattened spectra of cell free hemoglobin derivatives determined from the measured change in the light absorption of the sample within a wavelength range of 390-460 nm, and thereby determine the cell free hemoglobin concentration within the sample.

6. The method of claim 5 further comprising comparing the absorption spectrum at about the absorption maximum wavelength of cell-free hemoglobin derivatives to the flattened absorption spectrum of the cellular hemoglobin derivatives contained within erythrocytes and thereby determining the concentration of the cell-free hemoglobin derivatives.

7. The method of claim 5 further comprising, before the projecting step, selecting one or more wavelength ranges falling between 390 and 460 nm in which the absorbance of the cellular hemoglobin derivatives are flattened.

8. The method of claim 5 further comprising, before the projecting step, selecting one or more wavelength ranges falling between 390 and 460 nm in which the difference between the absorbance of cell-free hemoglobin derivatives and cellular hemoglobin derivatives contained within erythrocytes is maximal.

9. The method of claim 5 further comprising: measuring absorbance at about the wavelength of maximal absorbance characteristic for a hemoglobin derivative, measuring absorbance at least at one longer and one shorter wavelength, determining the differences in absorption, and thereby assessing the concentration of the hemoglobin derivative that is cell-free.

10. The method of claim 5 further comprising calculating the combined concentration of all cell-free hemoglobin derivatives, said combined concentration of cell-free hemoglobin also being calculated as a fraction of total hemoglobin, said total hemoglobin consisting of all cellular hemoglobin forms contained within erythrocytes plus all cell-free hemoglobin forms, and said total hemoglobin being measured by any established means known in the art.

11. The method of claim 10 further comprising calculating the concentration of hemoglobin contained within erythrocytes by subtracting from the measured total hemoglobin the calculated combined concentration of all cell-free hemoglobin.

12. A system for determining erythrocyte membrane fragility in a sample containing at least one cell-free hemoglobin derivative and at least one cellular hemoglobin derivative contained within erythrocytes, the system comprising:
a light source configured to emit light;
an erythrocyte stressor configured to apply a defined level of stress to the sample;
a sample block containing the sample, after it has received a defined level of stress from the erythrocyte stressor, and configured to allow the light to pass through the sample wherein, a first portion of the light, having a wavelength of about 390-460 nm, is absorbed by the cell-free hemoglobin derivatives, and a second portion of the light, having a wavelength of about 390-460 nm, is absorbed by the cellular hemoglobin derivatives contained within erythrocytes;
at least one absorption detector configured to determine the light absorption of the sample block containing the sample, within a wavelength range of about 390-460 nm, and to generate a flattened spectra of cellular hemoglobin derivatives contained within erythrocytes and a non-flattened spectra of cell-free hemoglobin derivatives; and
a processor configured to use data from the absorption detector to compare the flattened spectra of cellular hemoglobin derivatives contained within erythrocytes to the non-flattened spectra of cell free hemoglobin derivatives determined from the change in the light absorption of the sample within a wavelength range of 390-460 nm, and thereby determine the cell free hemoglobin concentration within the sample, said concentration then being used to calculate the fraction of cells which have become lysed under the defined level of stress, with said fraction representing erythrocyte membrane fragility.

13. The system of claim 12 wherein the hemoglobin derivatives are selected from the group consisting of oxyhemoglobin, deoxyhemoglobin, carboxyhemoglobin, and methemoglobin.

14. The system of claim 12 wherein the sample is a biological fluid selected from the group consisting of whole blood, anticoagulated blood, preserved blood, blood products, plasma, and serum.

15. The system of claim 12 wherein the first portion of light is absorbed by the cell-free hemoglobin derivatives providing an absorbance spectrum characteristic of hemoglobin in solution, and the second portion of absorbed light is absorbed by cellular hemoglobin derivatives contained within erythrocytes providing a flattened absorption spectrum characteristic of cellular hemoglobin derivatives.

16. A method for determining erythrocyte membrane fragility in a sample containing at least one cell-free hemoglobin derivative and at least one cellular hemoglobin derivative contained within erythrocytes, the method comprising:
stressing the sample with an erythrocyte stressor configured to apply a defined level of stress to the sample;
projecting light with a light source configured to emit light into a sample block containing the sample, which has been stressed, and configured to allow the light to pass through the sample wherein, a first portion of the light, having a wavelength of about 390-460 nm, is absorbed by the cell-free hemoglobin derivatives, and a second portion of the light, having a wavelength of about 390-460 nm, is absorbed by the cellular hemoglobin derivatives contained within erythrocytes;
measuring the light absorption with at least one absorption detector configured to determine the light absorption of the sample block containing the sample, within a wavelength range of about 390-460 nm, and to generate a flattened spectra of cellular hemoglobin derivatives contained within erythrocytes and a non-flattened spectra of cell-free hemoglobin derivatives; and utilizing a processor to compare the flattened spectra of cellular hemoglobin derivatives contained within erythrocytes to the non-flattened spectra of cell free hemoglobin derivatives determined from the measured change in the light absorption of the sample within a wavelength range of 390-460 nm, and thereby determine the cell free hemoglobin concentration within the sample, said concentration then being used to calculate the fraction of cells which have become lysed under the defined level of stress, with said fraction representing erythrocyte membrane fragility.

17. The method of claim 16 further comprising comparing the amount of cell-free hemoglobin derivatives before and after applying the erythrocyte stressor to the sample and thereby determining erythrocyte membrane fragility.

18. The method of claim 16 wherein the hemoglobin derivatives are selected from the group consisting of oxyhemoglobin, deoxyhemoglobin, carboxyhemoglobin, and methemoglobin.

19. The method of claim 16 wherein the sample is a biological fluid selected from the group consisting of whole blood, anticoagulated blood, preserved blood, blood products, plasma, and serum.

20. The method of claim 16 further comprising using a spectrophotometer to compare the non-flattened absorbance spectrum in the 390-460 nm region of cell-free hemoglobin derivatives and the flattened spectrum of hemoglobin derivatives contained within erythrocytes.

21. The method of claim 16 further comprising calculating an osmotic shear fragility index for the erythrocyte membranes in the sample.

22. The method of claim 16 further comprising determining changes in erythrocyte membrane fragility based on lysis of the erythrocytes in the sample by the stressor.

* * * * *